US008876853B2

United States Patent
Ren et al.

(10) Patent No.: US 8,876,853 B2
(45) Date of Patent: Nov. 4, 2014

(54) EMBOLIC PROTECTION SYSTEMS

(75) Inventors: Brooke Ren, Maple Grove, MN (US); James R. Lininger, Brooklyn Park, MN (US); Richard S. Kusleika, Eden Prairie, MN (US)

(73) Assignee: Covidien LP, Mansfield, MA (US)

( * ) Notice: Subject to any disclaimer, the term of this patent is extended or adjusted under 35 U.S.C. 154(b) by 584 days.

(21) Appl. No.: 12/621,988

(22) Filed: Nov. 19, 2009

(65) Prior Publication Data

US 2010/0063537 A1  Mar. 11, 2010

Related U.S. Application Data

(63) Continuation of application No. 11/715,266, filed on Mar. 7, 2007, now abandoned.

(60) Provisional application No. 60/781,059, filed on Mar. 10, 2006.

(51) Int. Cl.
| | |
|---|---|
| *A61F 2/01* | (2006.01) |
| *A61M 29/00* | (2006.01) |
| *A61M 25/00* | (2006.01) |
| *A61B 17/34* | (2006.01) |
| *A61F 2/06* | (2013.01) |
| *A61M 25/10* | (2013.01) |

(52) U.S. Cl.
CPC ............ *A61F 2/013* (2013.01); *A61M 25/0032* (2013.01); *A61F 2230/0006* (2013.01); *A61F 2230/0067* (2013.01); *A61B 2017/3484* (2013.01); *A61F 2002/061* (2013.01); *A61M 25/1002* (2013.01); *A61F 2002/018* (2013.01); *A61F 2230/008* (2013.01)
USPC ........................................................ 606/200

(58) Field of Classification Search
CPC . A61F 2/013; A61M 25/04; A61B 2017/348; A61B 2017/3484
USPC ................ 606/200, 192, 194, 110, 114, 127; 604/96.01, 509, 104–109, 93.01, 604/95.03, 97.01, 98.01, 99.01, 103.06; 600/115, 116, 127, 129
See application file for complete search history.

(56) References Cited

U.S. PATENT DOCUMENTS

| | | | |
|---|---|---|---|
| 4,389,208 A * | 6/1983 | LeVeen et al. | ............. 604/95.03 |
| 4,610,662 A | 9/1986 | Weikl et al. | |
| 4,636,195 A | 1/1987 | Wolinsky | |
| 4,645,493 A * | 2/1987 | Ferrando et al. | ............... 604/174 |
| 4,795,427 A * | 1/1989 | Helzel | ................ 604/9 |
| 4,824,436 A | 4/1989 | Wolinsky | |
| 4,986,810 A * | 1/1991 | Semrad | ......................... 604/106 |

(Continued)

*Primary Examiner* — Gregory Anderson
*Assistant Examiner* — Christopher L Templeton
(74) *Attorney, Agent, or Firm* — Alana T. Bergman, Esq.

(57) ABSTRACT

An embolic protection device comprising an expandable structure and a catheter. The catheter has a distal region and a working channel. The working channel has a working channel opening disposed in the distal region of the catheter, the working channel and the working channel opening are dimensioned to slideably receive an interventional device. The working channel has a distal region and at least a portion of the distal region of the working channel is disposed within the expandable structure. The expandable structure, when expanded in a first blood vessel, is able to stop blood flow through a second blood vessel and able to allow blood to flow through the first blood vessel. The working channel opening is able to be disposed to allow an interventional device to enter the second blood vessel.

25 Claims, 11 Drawing Sheets

(56) References Cited

U.S. PATENT DOCUMENTS

| | | | | |
|---|---|---|---|---|
| 4,997,435 A | * | 3/1991 | Demeter | 606/127 |
| 5,135,484 A | | 8/1992 | Wright | |
| 5,152,777 A | * | 10/1992 | Goldberg et al. | 606/200 |
| 5,163,906 A | | 11/1992 | Ahmadi | |
| 5,190,561 A | | 3/1993 | Graber | 606/127 |
| 5,267,960 A | * | 12/1993 | Hayman et al. | 604/106 |
| 5,328,470 A | | 7/1994 | Nabel et al. | |
| 5,380,284 A | | 1/1995 | Don Michael | |
| 5,397,307 A | | 3/1995 | Goodin | |
| 5,549,626 A | * | 8/1996 | Miller et al. | 606/200 |
| 5,558,642 A | | 9/1996 | Schweich, Jr. et al. | |
| 5,599,307 A | | 2/1997 | Bacher et al. | |
| 5,662,609 A | | 9/1997 | Slepian | |
| 5,728,133 A | | 3/1998 | Kontos | 606/213 |
| 5,800,394 A | * | 9/1998 | Yoon et al. | 604/101.05 |
| 5,833,650 A | | 11/1998 | Imran | |
| 5,908,407 A | | 6/1999 | Frazee et al. | |
| 5,911,725 A | | 6/1999 | Boury | |
| 5,947,985 A | | 9/1999 | Imran | |
| 5,968,064 A | * | 10/1999 | Selmon et al. | 606/189 |
| 5,997,557 A | * | 12/1999 | Barbut et al. | 606/159 |
| 6,071,263 A | * | 6/2000 | Kirkman | 604/104 |
| 6,126,635 A | | 10/2000 | Simpson et al. | |
| 6,306,163 B1 | * | 10/2001 | Fitz | 623/1.12 |
| 6,312,407 B1 | * | 11/2001 | Zadno-Azizi et al. | 604/103.03 |
| 6,312,444 B1 | | 11/2001 | Barbut | |
| 6,387,119 B2 | | 5/2002 | Wolf et al. | |
| 6,443,941 B1 | | 9/2002 | Slepian et al. | |
| 6,485,500 B1 | | 11/2002 | Kokish et al. | |
| 6,533,800 B1 | | 3/2003 | Barbut | |
| 6,569,146 B1 | | 5/2003 | Werner et al. | |
| 6,595,953 B1 | | 7/2003 | Coppi et al. | |
| 6,679,851 B2 | * | 1/2004 | Burbank et al. | 600/564 |
| 6,682,505 B2 | | 1/2004 | Bates et al. | |
| 6,689,097 B2 | | 2/2004 | Thramann | |
| 6,790,196 B2 | | 9/2004 | Kokate et al. | |
| 6,840,949 B2 | | 1/2005 | Barbut | |
| 6,887,227 B1 | | 5/2005 | Barbut | |
| 6,905,490 B2 | | 6/2005 | Parodi | |
| 6,908,474 B2 | * | 6/2005 | Hogendijk et al. | 606/200 |
| 6,936,057 B1 | | 8/2005 | Nobles | |
| 7,083,594 B2 | | 8/2006 | Coppi | |
| 7,232,452 B2 | * | 6/2007 | Adams et al. | 606/200 |
| 7,252,650 B1 | | 8/2007 | Andrews et al. | |
| 7,326,226 B2 | * | 2/2008 | Root et al. | 606/200 |
| 7,329,237 B2 | | 2/2008 | Yokoyama et al. | |
| 7,611,525 B2 | * | 11/2009 | Baig | 606/194 |
| 7,658,747 B2 | * | 2/2010 | Forde et al. | 606/200 |
| 7,927,347 B2 | * | 4/2011 | Hogendijk et al. | 606/200 |
| 7,935,075 B2 | * | 5/2011 | Tockman et al. | 604/34 |
| 8,034,095 B2 | * | 10/2011 | Randolph et al. | 623/1.12 |
| 2001/0047184 A1 | | 11/2001 | Connors, III | |
| 2002/0010418 A1 | | 1/2002 | Lary et al. | |
| 2002/0016565 A1 | | 2/2002 | Zadno-Azizi et al. | |
| 2002/0107479 A1 | | 8/2002 | Bates et al. | |
| 2002/0151870 A1 | * | 10/2002 | Grimes et al. | 604/509 |
| 2002/0165574 A1 | | 11/2002 | Ressemann et al. | |
| 2002/0169436 A1 | | 11/2002 | Gurm et al. | |
| 2002/0169458 A1 | | 11/2002 | Connors, III | |
| 2002/0173815 A1 | * | 11/2002 | Hogendijk et al. | 606/194 |
| 2003/0187495 A1 | | 10/2003 | Cully et al. | |
| 2004/0006306 A1 | | 1/2004 | Evans et al. | |
| 2004/0024448 A1 | | 2/2004 | Chang et al. | |
| 2005/0033334 A1 | | 2/2005 | Santra et al. | |
| 2005/0085770 A1 | | 4/2005 | Don Michael | |
| 2005/0124973 A1 | * | 6/2005 | Dorros et al. | 604/509 |
| 2005/0137622 A1 | * | 6/2005 | Griffin | 606/198 |
| 2005/0154443 A1 | | 7/2005 | Linder et al. | |
| 2005/0177186 A1 | | 8/2005 | Cully et al. | |
| 2005/0192620 A1 | | 9/2005 | Cully et al. | |
| 2005/0273051 A1 | | 12/2005 | Coppi | |
| 2006/0149350 A1 | | 7/2006 | Patel et al. | |
| 2006/0253186 A1 | | 11/2006 | Bates | |
| 2006/0259066 A1 | | 11/2006 | Euteneuer | |
| 2007/0021774 A1 | | 1/2007 | Hogendijk | |
| 2007/0150044 A1 | | 6/2007 | Wang et al. | |

* cited by examiner

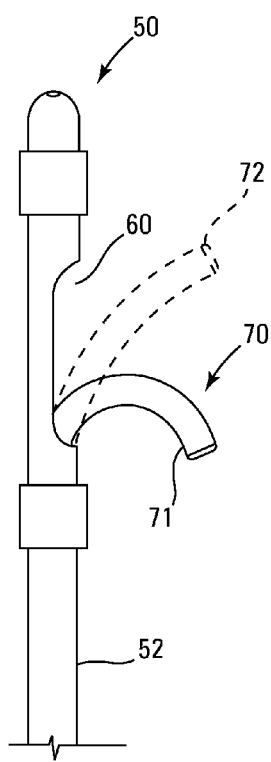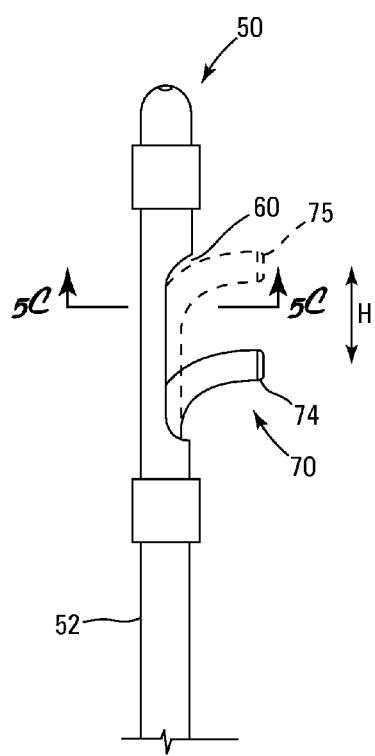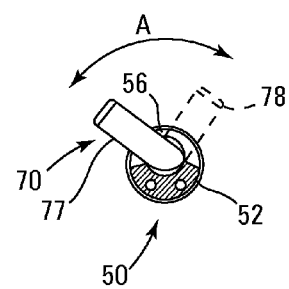
Fig. 5A
Fig. 5B
Fig. 5C

EMBOLIC PROTECTION SYSTEMS

This application is a continuation of U.S. application Ser. No. 11/715,266, filed Mar. 7, 2007, now abandoned, which claims the benefit of U.S. Provisional Application No. 60/781,059, filed Mar. 10, 2006, entitled "Embolic Protection Systems", the contents of each of which are hereby incorporated by reference herein.

FIELD OF THE INVENTION

The present invention relates to embolic protection systems. These embolic protection systems are particularly well-suited for use in branched blood vessels.

BACKGROUND OF THE INVENTION

Vessels are commonly treated to reduce or eliminate narrowings caused by arteriosclerotic disease. Interventional treatments can include use of balloon angioplasty, stenting, thrombectomy, atherectomy, and other procedures. During treatment particulate debris can be generated at the treatment site. Infarcts, strokes, and other major or minor adverse events are caused when debris embolizes into vasculature distal to the treatment site.

To prevent embolization of debris, embolic protection devices have been developed. During a procedure such devices can be placed distal or proximal to the treatment site. Embolic protection devices can remove emboli from the bloodstream by filtering debris from blood, by occluding blood flow followed by aspiration of debris, or can cause blood flow reversal to effect removal of debris. The shape, length and other characteristics of an embolic protection device are typically chosen based on the anatomical characteristics in the vicinity of the treatment site. However, some anatomies present specific challenges due to the anatomical shape or configuration. Known embolic protection devices are generally unsuitable for protection of vessels downstream of lesions at or near bifurcations because it is hard to protect both distal branches. Another challenging situation involves treatment of arteriosclerotic disease in branch vessels, for example at the ostium of renal arteries within the human body. Known embolic protection devices are generally unsuitable for protection of vessels downstream of lesions at or near the main renal artery because the artery is short and divides downstream into three or more additional branch vessels.

Accordingly, a need exists for an embolic protection device that will prevent embolization of debris generated at treatment sites within branch vessels.

SUMMARY OF THE INVENTION

According to one aspect of the present invention, an embolic protection device comprises an expandable structure and a catheter having a lumen. The expandable structure is expanded in a vessel run and the catheter is deployed in the vessel run and in or near the vessel branch. The expandable structure interrupts flow into the branch vessel and can permit flow in the vessel run. The catheter provides access to the branch vessel for treatment or diagnosis therein. The expandable structure may be a balloon, a membrane, or other structure. The embolic protection devices described herein are particularly well-suited for use in branched blood vessels, but they can also be used in straight blood vessels.

The invention provides an embolic protection device comprising an expandable structure and a catheter, the catheter having a distal region and having a working channel dimensioned to slideably receive an interventional device, the expandable structure being attached to the distal region of the catheter, the expandable structure having an expandable working channel extension and a working channel opening, the expandable working channel extension having a proximal end and a distal end, the proximal end of the working channel extension being attached to a distal end of the working channel, the distal end of the working channel extension forming the working channel opening, the working channel opening being disposed proximate an exterior surface of the expandable structure when the expandable structure is expanded, and the working channel, working channel extension, and the working channel opening forming a continuous lumen. In one embodiment, the expandable structure comprises a flow channel. In one embodiment, the expandable structure has a generally cylindrical shape, and in another embodiment, the expandable structure has a generally tubular shape.

The invention provides a method for positioning an embolic protection device within a patient's vasculature, the method comprising: providing an embolic protection device as described herein; advancing the embolic protection device to a target site within the patient's vasculature; and expanding the expandable structure within the patient's vasculature.

The invention provides an embolic protection device comprising an expandable structure and a catheter, the catheter having a distal region and having a working channel, the working channel having a working channel opening disposed in the distal region of the catheter, the working channel and the working channel opening dimensioned to slideably receive an interventional device, the working channel having a distal region, at least a portion of the distal region of the working channel being disposed within the expandable structure, the expandable structure, when expanded in a first blood vessel, is able to stop blood flow through a second blood vessel and able to allow blood to flow through the first blood vessel, and the working channel opening is able to be disposed to allow an interventional device to enter the second blood vessel.

It is to be understood that both the foregoing general description and the following detailed description are exemplary and explanatory and are intended to provide further explanation of the invention as claimed.

BRIEF DESCRIPTION OF THE DRAWINGS

The above and further advantages of the invention may be better understood by referring to the following description in conjunction with the accompanying drawings.

FIGS. 5A and 5B illustrate conceptually side view diagrams of catheters used in conjunction with an embolic protection system in accordance with the present invention.

FIG. 5C illustrates conceptually a partial cross-sectional diagram of catheters used in conjunction with an embolic protection system in accordance with the present invention.

DETAILED DESCRIPTION

Figure 1:
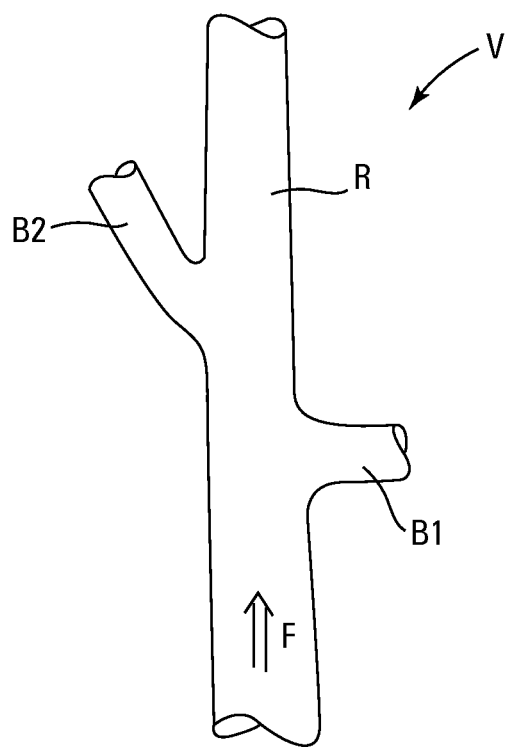
FIG. 1 illustrates conceptually a partial side view diagram of a vessel.

The terms "distal" and "proximal" as used herein refer to the relative position of the guidewire and catheters in a lumen. The most "proximal" point of the catheter is the end of the catheter extending outside the body closest to the physician. The most "distal" point of the catheter is the end of the catheter placed farthest into a body lumen from the entrance site.

The invention provides an embolic protection device comprising an expandable structure and a catheter, the catheter having a distal region and having a working channel dimensioned to slideably receive an interventional device, the expandable structure being attached to the distal region of the catheter, the expandable structure having an expandable working channel extension and a working channel opening, the expandable working channel extension having a proximal end and a distal end, the proximal end of the working channel extension being attached to a distal end of the working channel, the distal end of the working channel extension forming the working channel opening, the working channel opening being disposed proximate an exterior surface of the expandable structure when the expandable structure is expanded, and the working channel, working channel extension, and the working channel opening forming a continuous lumen. In one embodiment, the expandable structure comprises a flow channel. In one embodiment, the expandable structure has a generally cylindrical shape, and in another embodiment, the expandable structure has a generally tubular shape.

In embodiments of the invention, the catheter has a longitudinal axis and when the expandable structure is expanded, the flow channel has a cross-sectional area in a plane normal to the longitudinal axis that is 20 to 90 percent, 50 to 90 percent, or 75 to 90 percent of the cross-sectional area of the expandable structure. In one embodiment, the expandable structure is an actively expanded structure such as inflatable balloon. In one embodiment, the expandable structure is self-expanding. In one embodiment, the expandable structure is a mesh covered by a membrane. In another embodiment, the expandable structure is a laser-cut, open mesh nitinol tube covered by a thin layer of silicone polymer.

In one embodiment of the invention, the expandable structure, when expanded in a first blood vessel, is able to stop blood flow through a second blood vessel and able to allow blood to flow through the first blood vessel, and the working channel opening is able to be disposed to allow an interventional device to enter the second blood vessel. In one embodiment of the invention, the working channel extension and the working channel meet at an angle of from 75 to 105 degrees, and in another embodiment, the working channel extension and the working channel meet at an angle of approximately 90 degrees. In one embodiment, the catheter comprises a guidewire lumen.

In embodiments of the invention, the working channel has an internal diameter of from 0.030 cm to 0.51 cm, 0.10 cm to 0.28 cm, 0.15 cm to 0.24 cm, 0.23 cm, or 0.18 cm. In embodiments of the invention, the fully expanded working channel extension and the fully expanded working channel opening have an internal diameter of from 0.030 cm to 0.51 cm, 0.10 cm to 0.28 cm, 0.15 cm to 0.24 cm, 0.23 cm, or 0.18 cm. In one embodiment, one or more radiopaque marker bands are located near the distal end of the working channel. In another embodiment, one or more radiopaque marker bands are located near the distal end of the working channel extension. In one embodiment, the device further comprises a retractable sheath that can be placed over the expandable structure.

The invention provides a method for positioning an embolic protection device within a patient's vasculature, the method comprising: providing an embolic protection device as described herein; advancing the embolic protection device to a target site within the patient's vasculature; and expanding the expandable structure within the patient's vasculature. In one embodiment, the expandable structure is expanded in a first blood vessel, and stops blood flow through a second blood vessel and allows blood to flow through the first blood vessel, and the working channel opening is disposed to allow an interventional device to enter the second blood vessel. In another embodiment, a second catheter is introduced into the working channel, working channel extension, and working channel opening, and an interventional device is introduced into a lumen of the second catheter. In one embodiment, an interventional device is introduced into the second blood vessel and the blood in the second blood vessel is subsequently aspirated.

The invention provides an embolic protection device comprising an expandable structure and a catheter, the catheter having a distal region and having a working channel, the working channel having a working channel opening disposed in the distal region of the catheter, the working channel and the working channel opening dimensioned to slideably receive an interventional device, the working channel having a distal region, at least a portion of the distal region of the working channel being disposed within the expandable structure, the expandable structure, when expanded in a first blood vessel, is able to stop blood flow through a second blood vessel and able to allow blood to flow through the first blood vessel, and the working channel opening is able to be disposed to allow an interventional device to enter the second blood vessel. In one embodiment, the expandable structure comprises a flow channel. In another embodiment, the expandable structure has a generally tubular shape.

In one embodiment, the expandable structure comprises two expandable rings joined by a membrane. In another embodiment, the expandable structure is a mesh, the mesh having a portion covered by a membrane that prevents flow and having a portion not covered by a membrane so flow can occur through the mesh. This expandable structure may be self-expanding and the expandable structure may be a laser-cut, open mesh nitinol tube having a portion covered by a thin layer of silicone polymer.

In one embodiment, the expandable structure has a distal portion and a proximal portion, and when the expandable structure is expanded the distal portion is generally tubular and the proximal portion is tapered. In another embodiment, the expandable structure comprises three or more sealing arms, a membrane attached to the three or more sealing arms, and three or more support arms. The sealing arms may be made of self-expanding metal. The working channel opening may be disposed within the expandable structure. In one embodiment, the embolic protection device further comprises a second catheter that can be introduced into the working channel, working channel extension, and working channel opening, the second catheter having a lumen that can be used to deliver an interventional device.

In embodiments of the invention, the catheter has a longitudinal axis and when the expandable structure is expanded, the flow channel has a cross-sectional area in a plane normal to the longitudinal axis that is 20 to 90 percent, 50 to 90 percent, or 75 to 90 percent of the cross-sectional area of the expandable structure. In one embodiment, the expandable structure is an actively expanded structure such as inflatable balloon. In one embodiment, the expandable structure is self-expanding. In one embodiment, the expandable structure is a mesh covered by a membrane. In another embodiment, the expandable structure is a laser-cut, open mesh nitinol tube covered by a thin layer of silicone polymer. In one embodiment, the catheter comprises a guidewire lumen. In embodiments of the invention, the working channel has an internal diameter of from 0.030 cm to 0.51 cm, 0.10 cm to 0.28 cm, 0.15 cm to 0.24 cm, 0.23 cm, or 0.18 cm. In one embodiment, the device further comprises a retractable sheath that can be placed over the expandable structure.

FIG. 1 illustrates a partial side view diagram of vessel V in a body. Fluid flow travels through run R of vessel V. Branches B1 and B2 allow flow to divert from the flow direction F of the run so that flow can reach other parts of the body. Branch B1 is oriented at approximately 90 degrees to ("normal to") the run. Branch B2 is oriented at an angle to the run. Branches oriented at an angle to the run are commonly referred to as having a superior takeoff or as having an inferior takeoff from the run depending on how they are oriented. The invention described herein is suitable for use in vessels having branches with normal, inferior, or superior orientations to the run.

Figure 2A:
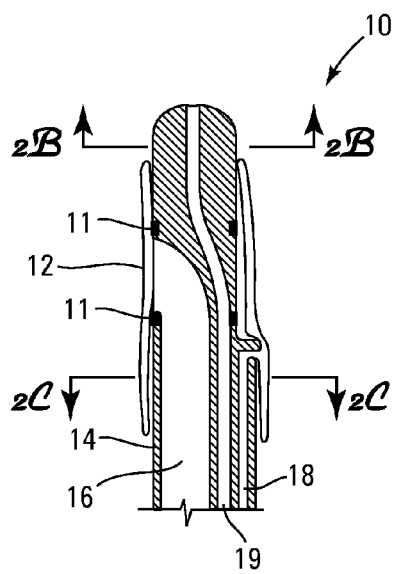
FIGS. 2A, 2B, and 2C illustrate conceptually partial cross-sectional diagrams of an embolic protection system in accordance with the present invention.
Figure 2D:
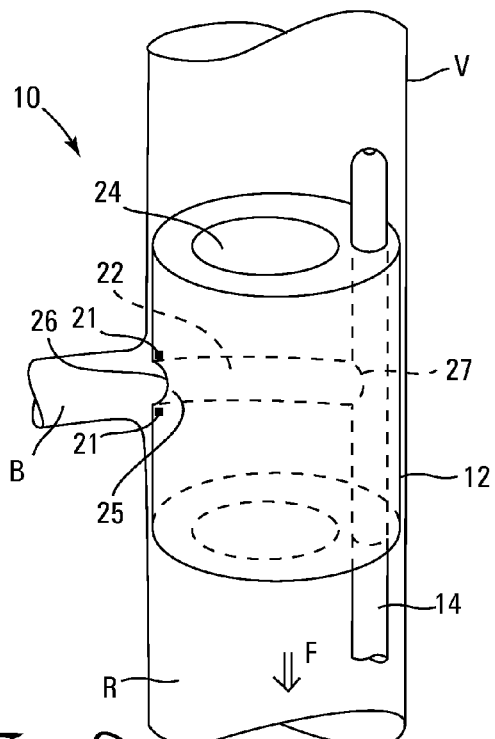
FIG. 2D illustrates conceptually an isometric diagram of an embolic protection system in accordance with the present invention.
Figure 2B:
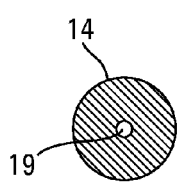
Figure 2C:
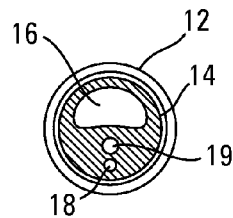
Figure 2E:
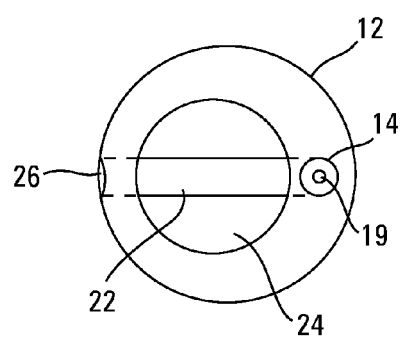
FIG. 2E illustrates conceptually a top view diagram of an embolic protection system in accordance with the present invention.

FIGS. 2A, 2B, 2C, 2D and 2E illustrate an embolic protection system in accordance with the present invention. FIG. 2A shows embolic protection system 10 comprised of expandable structure 12 and catheter 14 having a working channel 16, inflation lumen 18, and optional guidewire lumen 19. Catheter 14 can be comprised of polymers including but not limited to PEBAX®, polyethylene, nylon, polyester, and other materials known in the art, and may be made by processes known by those skilled in the art, such as extrusion. Preferably catheter 14 is torquable and comprises metal reinforcement, for example braided wire. FIG. 2B illustrates a cross sectional view of the tip region of catheter 14 having optional guidewire lumen 19. Guidewire lumen 19 is dimensioned to slideably receive guidewires (not shown) known in the art and can have an internal diameter ranging from 0.009 inch to 0.040 inch (0.023 cm to 0.010 cm). In one preferred embodiment, guidewire lumen 19 has a diameter of 0.021 inch (0.053 cm) and slideably receives 0.018 inch (0.046 cm) diameter guidewires. FIG. 2C illustrates a cross sectional view of the region of catheter 14 in the vicinity of expandable structure 12 having working channel 16, inflation lumen 18, and optional guidewire lumen 19. Working channel 16 is dimensioned to slideably receive interventional devices such as guidewires, balloon catheters, stent delivery systems with stents mounted thereon, atherectomy catheters, embolic protection devices such as distal embolic protection devices, thrombectomy devices, ultrasound catheters, aspiration catheters, and other devices (all not shown) known in that art and can have an internal diameter ranging from 0.012 inch to 0.200 inch (0.030 cm to 0.51 cm), more preferably from 0.040 inch to 0.110 inch (0.10 cm to 0.28 cm), more preferably from 0.060 inch to 0.096 inch (0.15 to 0.24 cm). In one preferred embodiment, working channel 16 has a diameter of 0.092 inch (0.23 cm). In another preferred embodiment, working channel 16 has a diameter of 0.070 inch (0.18 cm). A connector, for example a luer lock hub, may be attached to the proximal end of working channel 16 (not shown). One or more radiopaque marker bands 11 can be located on catheter 14 near the distal end of working channel 16. Radiopaque marker band 11 can comprise platinum, gold, tantalum, or other materials known in the art.

FIG. 2A illustrates embolic protection system 10 in which expandable structure 12 is unexpanded. FIG. 2D illustrates embolic protection system 10 in which expandable structure is expanded and positioned in vessel V having run R and branch B. Expandable structure 12 is comprised of working channel extension 22, optional flow channel 24, and working channel opening 26. Working channel extension 22 is bonded to expandable structure 12 at its distal most end 25 and is bonded to catheter 14 at its proximal most end 27 and may be comprised of a thin and strong membranous material such as biaxially oriented nylon, polyester, PEBAX®, and the like. Working channel extension 22 and working channel opening 26 are dimensioned to slideably receive interventional devices such as guidewires, balloon catheters, stent delivery systems with stents mounted thereon, atherectomy catheters, embolic protection devices such as distal embolic protection devices, thrombectomy devices, ultrasound catheters, aspiration catheters, and other devices (all not shown) known in that art and can have an internal diameter ranging from 0.012 inch to 0.200 inch (0.030 cm to 0.51 cm), more preferably from 0.040 inch to 0.110 inch (0.10 cm to 0.28 cm), more preferably from 0.060 inch to 0.096 inch (0.15 to 0.24 cm). In one preferred embodiment, working channel extension 22 has a diameter of 0.092 inch (0.23 cm). In another preferred embodiment, working channel extension 22 has a diameter of 0.070 inch (0.18 cm). One or more radiopaque marker bands 21 can be located on working channel extension 22 or expandable structure 12 near distal end of working channel extension 22. Radiopaque marker band 21 can comprise platinum, gold, tantalum, or other materials known in the art. Optional flow channel 24 is dimensioned to permit flow F through run R of vessel V when expandable structure 12 is expanded. In a plane normal to the direction of flow in run R, the lumenal area of optional flow channel 24 is preferably 20 to 90% of the run area in the same plane. In a preferred embodiment, the lumenal area of optional flow channel 24 is 50 to 90% of the run area. In a particularly preferred embodiment, the lumenal area of optional flow channel 24 is 75 to 90% of the run area.

Expandable structure 12 can be an inflatable balloon, a mesh covered by a membrane, or other structures and can be actively expanded, such as by expanding a balloon, or can be self expanding. Expandable structure 12 must remain in position when deployed and resist forces caused by flow F in vessel V and may comprise anchors (not shown) on the surface of expandable structure 12 such as barbs, hooks, surface roughness, or other anchoring geometries as are known in the art. In one embodiment, expandable structure 12 is a self-expanding, laser cut, open mesh nitinol tube covered with a thin membrane of silicone polymer and catheter 14 comprises a retractable sheath (not shown) positioned over expandable structure 12 so as to constrain expandable structure 12 during system 10 delivery to vessel V. In one embodiment, expandable structure 12 is an inflatable balloon and catheter 14 comprises inflation lumen 18 as illustrated in FIGS. 2A and 2C and the proximal end of inflation lumen 18 comprises a connector, for example a luer lock hub (not shown). The inflatable balloon 12 may be comprised of polyethylene, polyester, nylon, PEBAX®, silicone, latex, urethane, or other materials as are known in the art and may be inflated using saline, radiographic contrast media, mixtures of saline and radiographic contrast media, $CO_2$, or other fluids as are known in the art. In one preferred embodiment, expandable structure 12 is a nylon twelve balloon and is inflated using a mixture of 75% saline and 25% radiographic contrast media by volume.

Figure 3A:
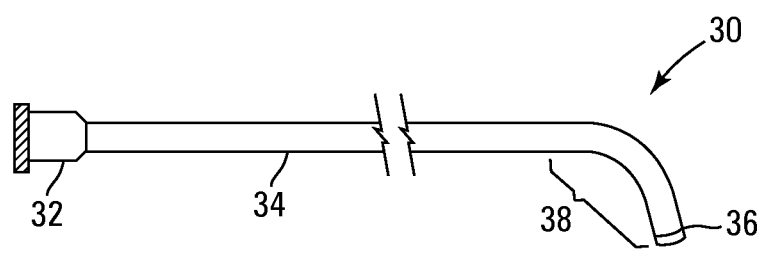
FIGS. 3A and 3B illustrate conceptually side view diagrams of catheters used in conjunction with an embolic protection system in accordance with the present invention.

FIG. 3A illustrates catheter 30 optionally used in conjunction with embolic protection system 10 in accordance with the present invention. Catheter 30 is comprised of hub 32, catheter shaft 34, and soft tip 36, and these three components are made of materials known in the art. As examples and not intended to be limiting, hub 32 may be comprised of polycarbonate or acrylic, catheter shaft 34 may be comprised of PEBAX®, polyethylene, nylon, or polyester, and soft tip 36 may be comprised of PEBAX®, urethane, silicone, or EVA (ethyl vinyl acetate). Catheter 30 is dimensioned to be slideably received within working channel 16, working channel extension 22, and working channel opening 26 of system 10. Distal region 38 of catheter 30 may be curved as illustrated in FIG. 3A and the exact curve will be chosen according to the intended use of device 10. In a preferred embodiment, distal region 38 of catheter 30 is comprised of a multipurpose curve as illustrated in FIG. 3A. In use, embolic protection system 10 is positioned in vessel V having branch B and catheter 30 is slideably advanced within working channel 16, working channel extension 22, and working channel opening 26 and positioned within or adjacent to branch B. Catheter 30 provides a smooth transition between the junction of working channel 16 and working channel extension 22 and in some embodiments reduces friction at this junction during subsequent advancement of interventional devices through system 10.

Figure 3B:
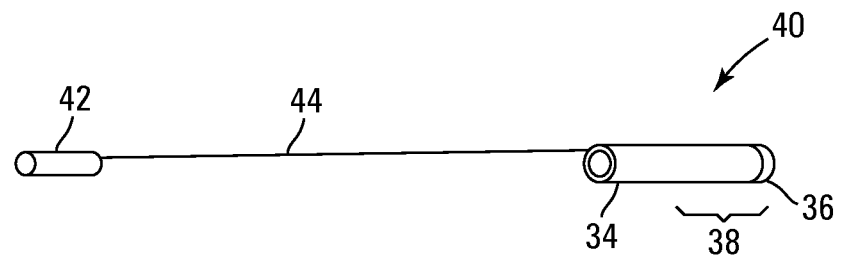

FIG. 3B illustrates catheter 40 optionally used in conjunction with an embolic protection system 10 in accordance with the present invention. Catheter 40 is comprised of handle 42, shaft 44, catheter shaft 34, soft tip 36, and these four components are made of materials known in the art. As examples and not intended to be limiting, handle 42 may be comprised of polycarbonate or acrylic, shaft 44 may be comprised of metal, PEEK (polyetheretherketone), liquid crystal polymer, or polyamide with or without metal reinforcement, and catheter 34 and soft tip 36 may be comprised of materials as described above. Catheter 40 is dimensioned to be slideably received within working channel 16, working channel extension 22, and working channel opening 26 of system 10. Distal region 38 of catheter 40 may be curved and the exact curve can be chosen according to the intended use of device 10. In some embodiments, catheter 40 distal region 38 is straight as shown in FIG. 3B. In use embolic protection system 10 is positioned in vessel V having branch B and catheter 40 is slideably advanced within working channel 16, working channel extension 22, and working channel opening 26 and positioned within or adjacent to branch B. Catheter 40 provides a smooth transition between the junction of working channel 16 and working channel extension 22 and in some embodiments reduces friction at this junction during subsequent advancement of interventional devices through system 10.

One non-limiting exemplary method of using embolic protection system 10 in accordance with the present invention is now described. Embolic protection system 10 is introduced into the arterial vasculature using conventional techniques, advanced over a known guidewire and positioned in run R of vessel V opposite branch B. Position of catheter 14 is adjusted using images of marker bands 11, 21 as guides until working channel opening 26 is located at desired location such as opposite branch B. To assist with positioning catheter 14, expandable structure 12 may be partially expanded and a second guidewire may be advanced through working channel 16, working channel extension 22, and working channel opening 26 into branch B, and then catheter 14 advanced, retracted, or torqued until alignment between branch B and working channel opening 26 is achieved. Expandable structure 12 is then fully expanded, for example in the case where expandable structure 12 is a balloon, by inflation, until flow into branch B is interrupted as confirmed by injection of radiographic contrast media through working channel 16, working channel extension 22, and working channel opening 26 into branch B. The second guidewire is removed from system 10.

Optionally, catheter 30 or 40 is advanced through working channel 16, working channel extension 22, and working channel opening 26 into or adjacent to branch B. An interventional guidewire is advanced through catheter 30 or 40 (if used) and through working channel 16, working channel extension 22, and working channel opening 26 into or beyond the region of interest of branch B, for example, distal to a lesion (not shown) in vessel branch B. Interventional devices such as angioplasty balloon catheters, stent delivery systems, and the like are advanced along the interventional guidewire and used to treat the region of interest of branch B. Embolic debris generated during treatment, if any, remains in the vicinity of the treatment area because there is no flow in branch B to transport the embolic material from the treatment area. Interventional devices are then removed.

An aspiration device, for example a syringe, preferably at least 30 cc capacity, is used to draw a vacuum and aspirate emboli from the vicinity of the treatment area proximally through working channel opening 26, working channel extension 22, and working channel 16 into the aspiration device. Alternatively, aspiration device can be attached to hub of catheter 30 (if used) and emboli can be aspirated from the vicinity of the treatment area proximally through catheter 30. Catheter 30 may be moved proximally and distally in the region of interest while aspiration is being applied to vacuum emboli from the region of interest.

After aspiration of emboli from the region of interest catheter 30 or 40 (if used) can be removed, expandable structure 12 can be unexpanded, for example in the case where expandable structure 12 is a balloon, by deflation, thereby restoring flow into branch B, and embolic protection system 10 can be removed from the patient.

In another non-limiting example, embolic protection system 10 can be used with a distal embolic protection device such as a filter or an occlusive device. After expansion of expandable structure 12, the distal embolic protection device is advanced through working channel 16 and through optional catheter 30 or 40 to a position distal to the region of interest, for example a stenotic lesion, in branch B, and then the distal protection device is deployed. Emboli generated during crossing of the stenotic lesion by the distal protection device remains in the vicinity of the stenotic lesion because there is no flow in branch B to transport the embolic material from the stenotic lesion area. Optionally, expandable structure 12 is then unexpanded at least in part, restoring flow into branch B in the example where a distal embolic protection filter is used. A distal embolic protection device such as a filter or an occlusive device can be used with any of the embodiments of the invention described herein.

In yet another non-limiting example, embolic protection system 10 can be used in conjunction with flow reversal techniques. After expansion of expandable structure 12, suction can be applied to the proximal end of working channel 16, to the proximal end of optional catheter 30 or 40, or to the proximal end of both, to cause blood to flow from branch B retrograde through working channel 16, the lumen of optional catheter 30 or 40, or both. The interventional procedure can then be performed and any emboli generated during the procedure will be transported by the retrograde flow proximally from the treatment site until removed from the body. Flow reversal techniques can be used with any of the embodiments of the invention described herein.

Figure 4A:
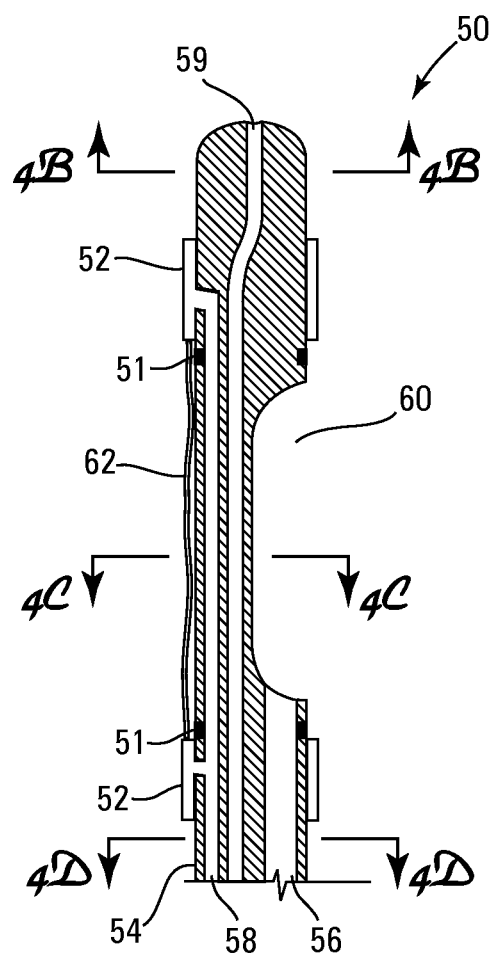
FIGS. 4A, 4B, 4C, and 4D illustrate conceptually cross-sectional diagrams of an embolic protection system in accordance with the present invention.
Figure 4B:
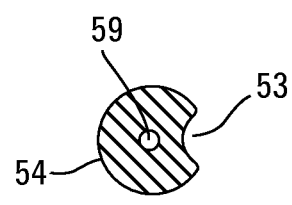
Figure 4C:
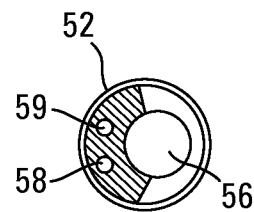
Figure 4D:
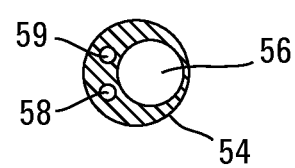

FIGS. 4A, 4B, 4C, 4D, and 4F illustrate an embolic protection system in accordance with the present invention. FIG. 4A shows embolic protection system 50 comprised of expandable structures 52 and catheter 54 having a working channel 56, inflation lumen 58, and optional guidewire lumen 59. Catheter 54 can be comprised of polymers including but not limited to PEBAX®, polyethylene, nylon, polyester, and other materials known in the art, and may be made by processes known by those skilled in the art, such as extrusion. Preferably catheter 54 is torquable and is comprised of metal reinforcement, for example braided wire. FIG. 4B illustrates a cross sectional view of the tip region of catheter 54 having optional guidewire lumen 59. Guidewire lumen 59 is dimensioned to slideably receive guidewires (not shown) known in the art and can have an internal diameter ranging from 0.009 inch to 0.040 inch (0.02 cm to 0.10 cm). In one preferred embodiment, guidewire lumen 59 has a diameter of 0.021 inch (0.053 cm) and slideably receives 0.018 inch (0.46 cm) diameter guidewires. The catheter tip optionally has depression 53 which is sized to allow a guidewire (not shown) oriented parallel to the length of catheter 54 to fit into depression without increasing the overall outside diameter of catheter 54. Depression 53 extends along outside surface of catheter 54 from distal end of opening 60 to tip of catheter 54. FIG. 4C illustrates a cross sectional view of the region of catheter 54 in the vicinity of opening 60 having inflation lumen 58 and optional guidewire lumen 59. FIG. 4D illustrates a cross sectional view of the shaft region of catheter 54 having working channel 56, inflation lumen 58, and optional guidewire lumen 59. Working channel 56 is dimensioned to slideably receive interventional devices such as guidewires, balloon catheters, stent delivery systems with stents mounted thereon, atherectomy catheters, embolic protection devices such as distal embolic protection devices, thrombectomy devices, ultrasound catheters, aspiration catheters, and other devices (all not shown) known in that art and can have an internal diameter ranging from 0.012 inch to 0.200 inch (0.030 cm to 0.51 cm), more preferably from 0.040 inch to 0.110 inch (0.10 cm to 0.28 cm), more preferably from 0.060 inch to 0.096 inch (0.15 to 0.24 cm). In one preferred embodiment, working channel 56 has a diameter of 0.092 inch (0.23 cm). In another preferred embodiment, working channel 56 has a diameter of 0.070 inch (0.18 cm). A connector, for example a luer lock hub, may be attached to the proximal end of working channel 56 (not shown). One or more radiopaque marker bands 51 can be located on catheter 54 near either or both ends of opening 60. Radiopaque marker band 51 can comprise platinum, gold, tantalum, or other materials known in the art.

Figure 4E:
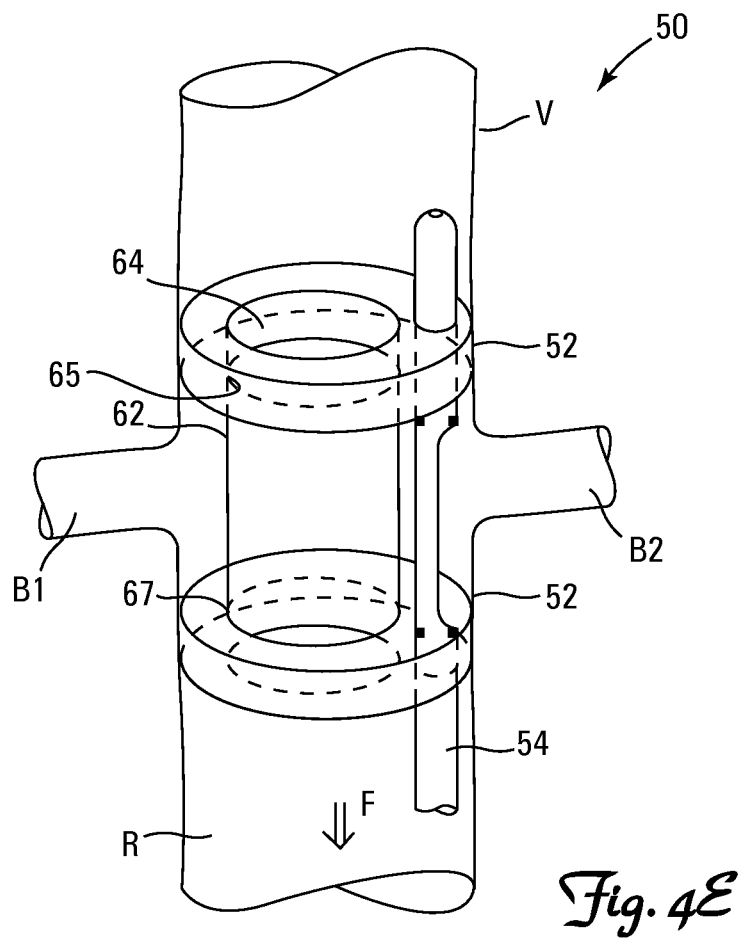
FIG. 4E illustrates conceptually an isometric diagram of an embolic protection system in accordance with the present invention.
Figure 4F:
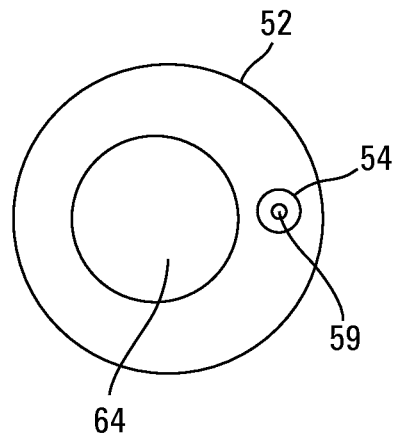
FIG. 4F illustrates conceptually a top view diagram of an embolic protection system in accordance with the present invention.

FIG. 4A illustrates embolic protection system 50 in which expandable structures 52 are unexpanded. FIG. 4E illustrates embolic protection system 50 in which expandable structures 52 are expanded and positioned in vessel V having run R and branches B1 and B2. Expandable structures 52 are comprised of optional flow channel 64 defined by membrane 62. Membrane 62 is permanently attached to expandable structures 52 at its distal most end 65 and at its proximal most end 67 and may be comprised of a thin and strong membranous material such as biaxially oriented nylon, polyester, PEBAX®, and the like. Optional flow channel 64 is dimensioned to permit flow F through run R of vessel V when expandable structures 52 are expanded. In a plane normal to the direction of flow in run R, the lumenal area of optional flow channel 64 is preferably 20 to 90% of the run area in the same plane. In a preferred embodiment, the lumenal area of optional flow channel 64 is 50 to 90% of the run area. In a particularly preferred embodiment, the lumenal area of optional flow channel 64 is 75 to 90% of the run area.

Expandable structures 52 can be an inflatable balloon, a mesh covered by a membrane, or other structures and can be actively expanded, such as by expanding a balloon, or can be self expanding. Expandable structures 52 must remain in position when deployed and resist forces caused by flow F in vessel V and may comprise anchors (not shown) on the surface of expandable structures 52 such as barbs, hooks, surface roughness, or other anchoring geometries as are known in the art. In one embodiment, expandable structures 52 are self-expanding, laser cut, open mesh nitinol tubes covered with thin membranes of silicone polymer and catheter 54 comprises a retractable sheath (not shown) positioned over expandable structures 52 so as to constrain expandable structures 52 during system 50 delivery to vessel V. In one embodiment, expandable structures 52 are inflatable balloons, catheter 54 comprises inflation lumen 58 as illustrated in FIGS. 4A, 4C and 4D, and the proximal end of inflation lumen 58 comprises a connector, for example a luer lock hub (not shown). The inflatable balloon 52 may be comprised of polyethylene, polyester, nylon, PEBAX®, silicone, latex, urethane, or other materials as are known in the art and may be inflated using saline, radiographic contrast media, mixtures of saline and radiographic contrast media, $CO_2$, or other fluids as are known in the art. In one preferred embodiment, expandable structures 52 are nylon twelve balloons and are inflated using a mixture of 75% saline and 25% radiographic contrast media by volume.

FIGS. 5A and 5B illustrate catheters used in conjunction with an embolic protection system in accordance with the present invention. For convenience expandable elements are shown in an unexpanded state in these illustrations. It is understood that expandable elements 52 will preferably be expanded during use of catheters 70 in conjunction with embolic protection system 50.

FIGS. 5A, 5B, and 5C illustrate catheter 70 inserted into catheter 52 through working channel 56 and extending out of opening 60. Catheter 70 may be an interventional catheter such as a guide catheter, balloon catheter, stent delivery system with stent mounted thereon, atherectomy catheter, embolic protection device such as distal embolic protection device, thrombectomy device, ultrasound catheter, aspiration catheter, or other device (all not shown) known in the art. Catheter 70 may be an interventional catheter such as catheter 30 or catheter 40 described previously in this document. In one preferred embodiment, catheter 70 is a steerable guide catheter. In another preferred embodiment, catheter 70 is a non-steerable guide catheter. FIG. 5A shows catheter 70 oriented properly 71 for use with a branch vessel having an inferior takeoff and in phantom shows catheter 70 oriented properly 72 for use with a branch vessel having an superior takeoff. FIG. 5B illustrates catheter 70 oriented properly for use with a branch vessel having a normal takeoff and shows that the position of catheter 70 can be adjusted vertically between position 74 and phantom position 75 over vertical range of motion H. FIG. 5C illustrates that the position of catheter 70 can be adjusted angularly between position 77 and phantom position 78 over angular range of motion A. Embolic protection system 50 can be used with a broad range of vessel anatomies because the position of catheter 70 can be adjusted relative to the orientation of branch vessels B so as to facilitate passage of interventional catheters from working channel 56 to lumen of branch B.

One non-limiting exemplary method of using embolic protection system 50 in accordance with the present invention is now described. Embolic protection system 50 is introduced into the arterial vasculature using conventional techniques, advanced over a known guidewire and positioned in run R of vessel V opposite branch B2. Position of catheter 54 is adjusted using images of marker bands 51 as guides until opening 60 is located at desired location such as opposite branch B2. To assist with positioning catheter 54, expandable structures 52 may be partially expanded and a second guidewire may be advanced through working channel 56 into branch B2 and catheter 54 advanced, retracted, or torqued until alignment between branch B2 and opening 60 is achieved. Expandable structures 52 are then fully expanded, for example in the case where expandable structures 52 are balloons, by inflation, until flow into branch B2 is interrupted as confirmed by injection of radiographic contrast media through working channel 56 into branch B2. The second guidewire is removed from system 50.

Optionally, catheter 70 is advanced through working channel 56 into or adjacent to branch B2. An interventional guidewire is advanced through catheter 70 into or beyond the region of interest within branch B2. Interventional devices such as angioplasty balloon catheters, stent delivery systems, and the like are advanced along the interventional guidewire and used to treat the region of interest within branch B2. Embolic debris generated during treatment, if any, remains in the vicinity of the treatment area because there is no flow in branch B2 to transport the embolic material from the treatment area. Interventional devices are removed after treatment.

An aspiration device, for example a syringe, preferably at least 30 cc capacity, is used to draw a vacuum and aspirate emboli from the vicinity of the treatment area proximally through working channel 56 into the aspiration device. Alternatively, aspiration device can be attached to hub of catheter 70 (if used) and emboli can be aspirated from the vicinity of the treatment area proximally through catheter 70. Catheter 70 may be moved proximally and distally in the region of interest while aspiration is being applied to vacuum emboli from the region of interest.

After aspiration of emboli from the region of interest, catheter 70 can be removed, expandable structures 52 can be unexpanded, for example in the case where expandable structures 52 comprise balloons, by deflation, thereby restoring flow into branch B2, and embolic protection system 50 can be removed from the patient.

An alternative method of delivering embolic protection system 50 in accordance with the present invention is now described. A guidewire is introduced into branch B2 using conventional techniques. Embolic protection system 50 is backloaded over the guidewire by inserting the proximal end of the guidewire into opening 60 and working channel 56 of catheter 54. The guidewire is pressed into depression 53 and introduced into the arterial vasculature through a known introducer, and then advanced over the guidewire and positioned in run R of vessel V opposite branch B2. If desired, a second guidewire can be loaded through optional guidewire lumen 59 and the tip of second guidewire extended slightly out of distal end of catheter 54 tip to facilitate advancement of embolic protection system 50 through the vasculature. The position of catheter 54 is adjusted using images of marker bands 51 as guides until opening 60 is located at desired location such as opposite branch B2. Expandable structures 52 are then fully expanded until flow into branch B2 is interrupted as confirmed by injection of radiographic contrast media through working channel 56 into branch B2. The guidewire and second guidewire may be removed from system 50.

Figure 6A:
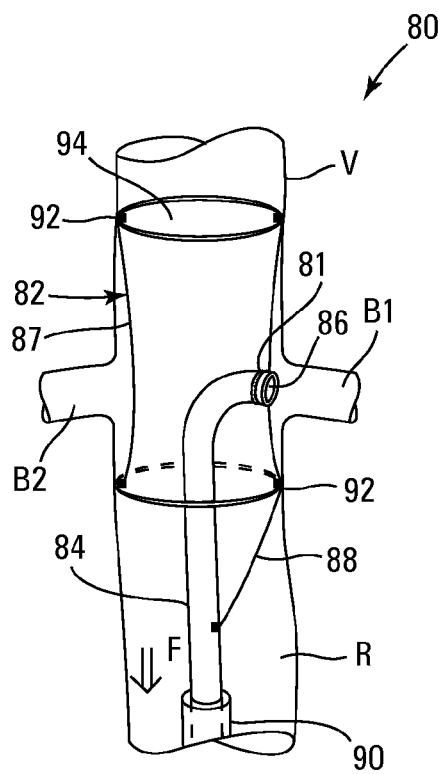
FIG. 6A illustrates conceptually an isometric diagram of an embolic protection system in accordance with the present invention.
Figure 6B:
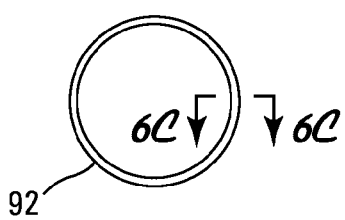
FIGS. 6B, 6D, and 6E illustrate conceptually plan view diagrams of components of an embolic protection system in accordance with the present invention.
Figure 6C:
FIG. 6C illustrates conceptually a cross-sectional diagram of a component of an embolic protection system in accordance with the present invention.
Figure 6D:
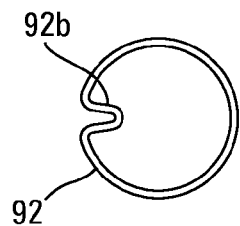

FIGS. 6A, 6B, 6C, 6D, and 6E illustrate conceptually an alternative embodiment of an embolic protection system in accordance with the present invention. FIG. 6A shows embolic protection system 80 comprised of expandable structures 82, membrane 87, and catheter 84 having a working channel 86, tether 88, and sheath 90. Catheter 84 can be comprised of polymers including but not limited to PEBAX®, polyethylene, nylon, polyester, and other materials known in the art, and may be made by processes known by those skilled in the art, such as extrusion. Preferably catheter 84 is torquable and is comprised of metal reinforcement, for example braided wire. Working channel 86 is dimensioned to slideably receive interventional devices such as guidewires, balloon catheters, stent delivery systems with stents mounted thereon, atherectomy catheters, embolic protection devices such as distal embolic protection devices, thrombectomy devices, ultrasound catheters, aspiration catheters, and other devices (all not shown) known in that art and can have an internal diameter ranging from 0.012 inch to 0.200 inch (0.030 cm to 0.51 cm), more preferably from 0.040 inch to 0.110 inch (0.10 cm to 0.28 cm), more preferably from 0.060 inch to 0.096 inch (0.15 to 0.24 cm). In one preferred embodiment, working channel 86 has a diameter of 0.092 inch (0.23 cm). In another preferred embodiment, working channel 86 has a diameter of 0.070 inch (0.18 cm). A connector, for example a luer lock hub, may be attached to the proximal end of working channel 86 (not shown). One or more radiopaque marker bands 81 can be located on catheter 84 near distal end of working channel 86. Radiopaque marker band 81 can comprise platinum, gold, tantalum, or other materials known in the art. Tether 88 can be comprised of material having high tensile strength such as metal, suture, KEVLAR®, polyester, nylon, or other materials and may comprise molecules oriented along the length of the tether. One preferred material is stranded nitinol wire.

Another preferred tether material is oriented DACRON® suture. Sheath 90 can be comprised of polymers including but not limited to PEBAX®, polyethylene, nylon, polyester, and other materials known in the art, and may be made by processes known by those skilled in the art, such as extrusion. Preferably, sheath 90 is torqueable and is comprised of metal reinforcement, for example braided wire. Sheath 90 is dimensioned to slideably receive catheter 84, tether 88, expandable structure 82, and membrane 87.

Expandable structure 82 comprises rings 92 and flow channel 94 defined by membrane 87 and inner perimeter of rings 92. Membrane 87 is permanently attached to rings 92 and to distal end of catheter 84 and may be comprised of a thin and strong membranous material such as biaxially oriented nylon, polyester, PEBAX®, and the like. Flow channel 94 is dimensioned to permit flow F through run R of vessel V when expandable structure 82 is expanded. In a plane normal to the direction of flow in run R, the lumenal area of flow channel 94 is preferably 20 to 90% of the run area in the same plane. In a preferred embodiment, the lumenal area of flow channel 94 is 50 to 90% of the run area. In a particularly preferred embodiment, the lumenal area of flow channel 94 is 75 to 90% of the run area.

Figure 6E:
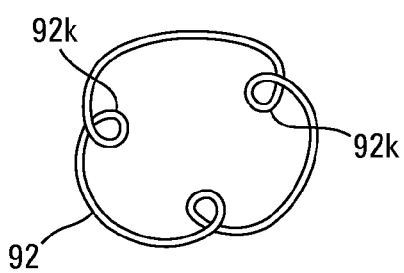

Expandable structure 82 can be an elastic material pre-set in an expanded shape, an elastic mesh, a laser cut, open mesh nitinol tube, or other structures and in a preferred embodiment are self-expanding. Expandable structure 82 must remain in position when deployed and resist forces caused by flow F in vessel V and may comprise anchors (not shown) on the surface of expandable structure 82 such as barbs, hooks, surface roughness, or other anchoring geometries as are known in the art. In one embodiment, expandable structure 82 comprises rings 92 of superelastic nitinol wire of a circular cross section heat set into an expanded shape, illustrated in FIGS. 6B and 6C. In one embodiment, a ring 92 comprises at least one beak 92b formed into the structure (FIG. 6D), and in still another embodiment a ring 92 comprises at least one loop 92k formed into the structure (FIG. 6E). Beak 92b and loop 92k facilitate folding of rings 92 so that they can be slideably received into sheath 90.

Figure 7A:
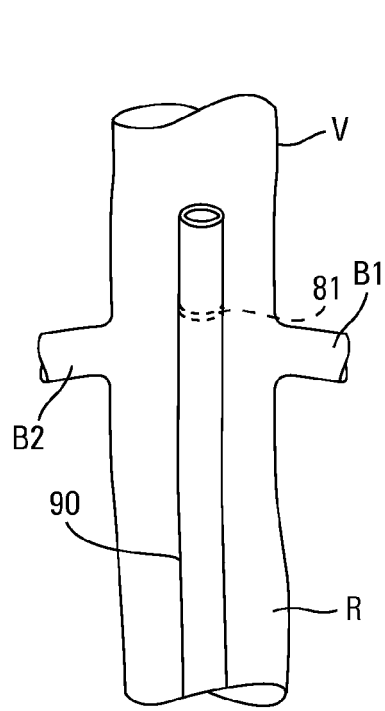
FIGS. 7A, 7B, 7C, and 7D illustrate conceptually a method of using an embolic protection system in accordance with the present invention.
Figure 7B:
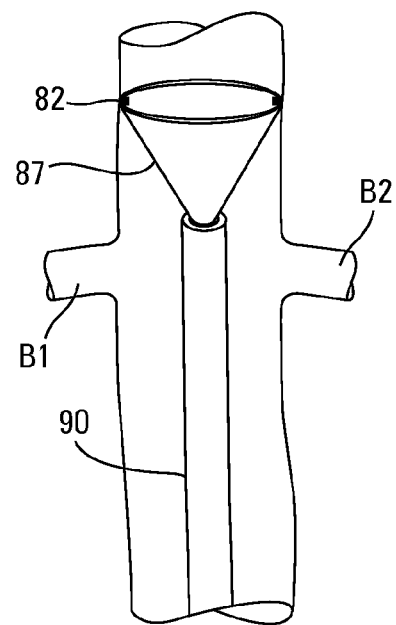
Figure 7C:
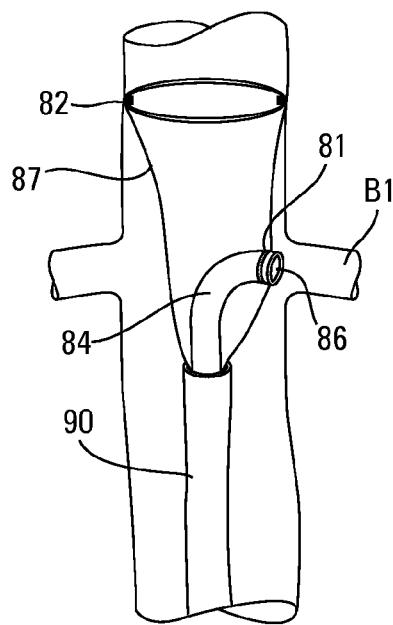

With reference to FIGS. 7A, 7B, 7C, and 7D, a non-limiting exemplary method of using embolic protection system 80 in accordance with the present invention is now described. Embolic protection system 80 is introduced into the arterial vasculature using conventional techniques, advanced through the vasculature and positioned in run R of vessel V opposite branch B1. Position of sheath 90 is adjusted using images of marker band 81 as a guide until marker band 81 is located at desired location such as superior to branch B1 (FIG. 7A). Distal most expandable structure 82 is then expanded by withdrawing sheath 90 relative to catheter 84 (FIG. 7B). Further withdrawal of sheath 90 relative to catheter 84 exposes catheter tip (FIG. 7C). Catheter 84, sheath 90, or both are then rotated by applying torsion on their respective shafts to assure that channel 86 is desirably aligned relative to branch B1. Radiographic contrast media can be injected through channel 86 to further ascertain orientation of catheter 84 tip relative to lumen of branch B1.

Figure 7D:
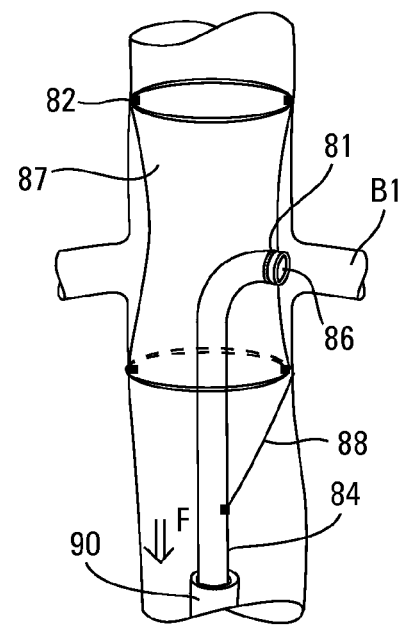

Once satisfied with orientation of catheter 84 tip relative to lumen of branch B1 sheath 90 is further withdrawn relative to catheter 84 until the proximal most portion of expandable structure 82 is expanded and tether 88 is fully outside of sheath 90 (FIG. 7D). When both distal most and proximal most portions of expandable structure 82 are expanded, flow F in run R of vessel V is prevented from entering branch B1.

An interventional guidewire is now advanced through catheter 84 into or beyond the region of interest of branch B1. Optionally, catheter 30, 40, or 70 is advanced through working channel 86 into or adjacent to branch B1 either before, during, or after advancement of the interventional guidewire. Interventional devices such as angioplasty balloon catheters, stent delivery systems, and the like are advanced along the interventional guidewire and used to treat the region of interest of branch B1. Embolic debris generated during treatment, if any, remains in the vicinity of the treatment area because there is no flow in branch B1 to transport the embolic material from the treatment area. Interventional devices are removed after treatment.

An aspiration device, for example a syringe, preferably at least 30 cc capacity, is used to draw a vacuum and aspirate emboli from the vicinity of the treatment area proximally through working channel 86 into the aspiration device. Alternatively, the aspiration device can be attached to hub of catheter 30, 40, or 70 (if used) and emboli can be aspirated from the vicinity of the treatment area proximally through catheter 30, 40, or 70. Catheter 30, 40, or 70 may be moved proximally and distally in the region of interest while aspiration is being applied to vacuum emboli from the region of interest.

After aspiration of emboli from the region of interest catheter 30, 40, or 70 can be removed, expandable structure 82 can be unexpanded by advancing sheath 90 over catheter 84, causing tether 88 to enter sheath, followed by collapse of the proximal most portion of expandable structure 82, membrane 87, and the distal most portion of expandable structure 82. Optional beak or eyelets, if used, reduce the amount of force needed to collapse expandable structure 82. Sheath 90 causes the curvature of catheter 84 to be straightened as the catheter enters the sheath. As embolic protection system 80 is collapsed into sheath 90, flow into branch B1 is restored. Embolic protection system 80 can thereafter be removed from the patient.

Figures 8A, 8B:
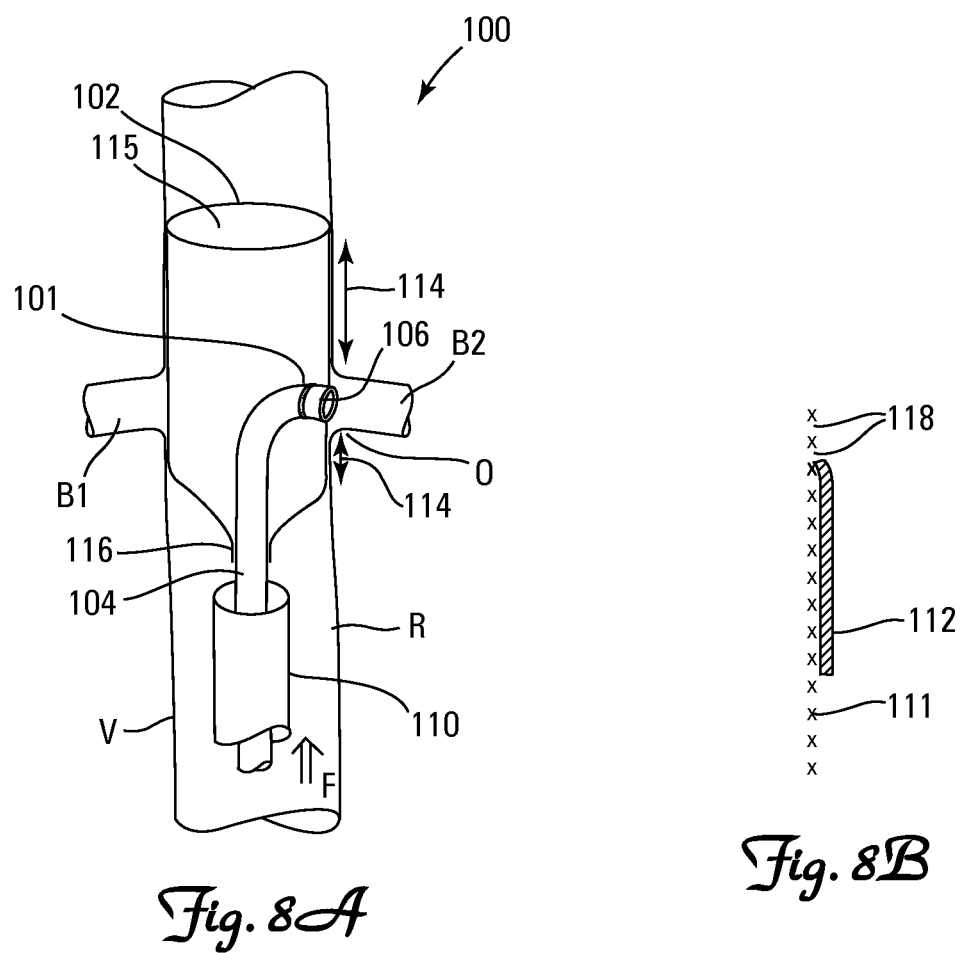
FIG. 8A illustrates conceptually an isometric diagram of an alternative embodiment of an embolic protection system in accordance with the present invention.
FIG. 8B illustrates conceptually a cross-sectional diagram of a component of an embolic protection system in accordance with the present invention.

FIGS. 8A and 8B illustrate an alternative embodiment of an embolic protection system in accordance with the present invention. Embolic protection system 100 is comprised of expandable structure 102 and catheter 104 having working channel 106 and sheath 110. Catheter 104 can be comprised of polymers including but not limited to PEBAX®, polyethylene, nylon, polyester, and other materials known in the art, and may be made by processes known by those skilled in the art, such as extrusion. Preferably catheter 104 is torquable and is comprised of metal reinforcement, for example braided wire. Working channel 106 is dimensioned to slideably receive interventional devices such as guidewires, balloon catheters, stent delivery systems with stents mounted thereon, atherectomy catheters, embolic protection devices such as distal embolic protection devices, thrombectomy devices, ultrasound catheters, aspiration catheters, and other devices (all not shown) known in the art and can have an internal diameter ranging from 0.012 inch to 0.200 inch (0.030 cm to 0.51 cm), more preferably from 0.040 inch to 0.110 inch (0.10 cm to 0.28 cm), more preferably from 0.060 inch to 0.096 inch (0.15 to 0.24 cm). In one preferred embodiment, working channel 106 has a diameter of 0.092 inch (0.23 cm). In another preferred embodiment, working channel 106 has a diameter of 0.070 inch (0.18 cm). A connector, for example a luer lock hub, may be attached to proximal end of working channel 106 (not shown). One or more radiopaque marker bands 101 can be located on catheter 104 near the distal end of working channel 106. Radiopaque marker band 101 can comprise platinum, gold, tantalum, or other materials known in the art. Sheath 110 can be comprised of polymers including but not limited to PEBAX®, polyethylene, nylon, polyester, and other materials known in the art, and may be made by processes known by those skilled in the art, such as extrusion.

Preferably sheath 110 is torqueable and is comprised of metal reinforcement, for example braided wire. Sheath 110 is dimensioned to slideably receive catheter 104 and expandable structure 102. Optionally, the distal portion of sheath 110 is keyed to catheter 104 by means of a key and keyway, linearly slideable non-circular cross sections, or other means (all not shown) to prevent the distal portion of sheath 110 from rotating in relation to catheter 104.

Expandable structure 102 is comprised of mesh 111, membrane 112, and flow channel 115. Mesh 111 is attached to catheter 104 at location 116 using techniques such as bonding, welding, fusing, solvent bonding, ultrasonic welding, and the like. Mesh openings 118 are dimensioned to allow flow of fluids through mesh, and mesh open area is defined as the combined area of all mesh openings not apposed to wall of vessel V and not covered by membrane 112 in the portion of mesh deployed outside of sheath 110. Mesh 111 is preferably made of self-expanding metal such as ELGILOY®, stainless steel, cobalt-chromium alloy, superelastic alloy, nitinol, or other materials as are known in the art. Mesh 111 may be fabricated using techniques such as braiding of wires or filaments, knitting of wires or filaments, laser cutting of tubes, perforation of sheet, welding of component parts, heat treatment, or other methods. In a preferred embodiment, mesh 111 is comprised of braided nitinol wires heat set in an expanded shape. Membrane 112 is permanently attached to mesh 111 and to distal end of catheter 104 and may be attached to outer diameter of mesh, inner diameter of mesh, through the thickness of the mesh, or any combination thereof. Membrane 112 is comprised of a thin and strong membranous material such as biaxially oriented nylon, polyester, PEBAX®, of thin flexible materials such as silicone, polyurethane, latex, and the like. In a preferred embodiment, membrane 112 is comprised of silicone polymer of 90 Shore A durometer or less and is attached to the inner diameter of mesh 111. Membrane 112 may be attached to a portion of or to all of mesh 111. In a preferred embodiment, membrane 112 is attached to mesh in the region 114 extending from near the tip of catheter 104 to a distance away from ostium O of branch B2 of vessel V. Flow channel 115 and mesh open area are dimensioned to permit flow F through run R of vessel V when expandable structure 102 is expanded. In a plane normal to the direction of flow in run R, the lumenal area of flow channel 115 is preferably 20 to 90% of the run area in the same plane. In a preferred embodiment, the lumenal area of flow channel 115 is 50 to 90% of the run area. In a particularly preferred embodiment, the lumenal area of flow channel 115 is 75 to 90% of the run area.

Expandable structure 102 must remain in position when deployed and resist forces caused by flow F in vessel V and may comprise anchors (not shown) on the surface of expandable structure 102 such as barbs, hooks, surface roughness, or other anchoring geometries as are known in the art. While expandable structure 102 is shown as a cylinder with a conical end in FIG. 8A, expandable structure 102 can have many shapes without departing from the spirit and scope of the invention. In one embodiment, expandable structure 102 is made of superelastic nitinol wire of a circular cross section heat set into an expanded shape.

One non-limiting exemplary method of using embolic protection system 100 in accordance with the present invention is now described. Embolic protection system 100 is introduced into the arterial vasculature using conventional techniques, advanced through the vasculature and positioned in run R of vessel V opposite branch B2. The position of system 100 is adjusted using images of marker band 101 as a guide until marker band 101 is located at desired location such as superior to branch B2. The distal most portion of expandable structure 102 is then expanded by withdrawing sheath 110 relative to catheter 104. Flow F will pass through flow channel 115 including through mesh open area, allowing catheter 104 to be more accurately positioned since there will be fewer flow generated forces altering the position of system 100. Further withdrawal of sheath 110 relative to catheter 104 exposes the catheter tip. Catheter 104, sheath 110, or both are then rotated by applying torsion on their respective shafts to assure that working channel 106 is desirably aligned relative to branch B2. Radiographic contrast media can be injected through working lumen 106 to further ascertain orientation of catheter 104 tip relative to lumen of branch B2.

Once satisfied with the orientation of catheter 104 tip relative to lumen of branch B2, sheath 110 is further withdrawn relative to catheter 104 until proximal portion of expandable structure 102 is expanded and fully outside of sheath 110, allowing membrane 112 to be pressed against wall of vessel V. When both expandable structure 102 is expanded and membrane 112 abuts vessel V in the region of ostium O of branch B2, flow F in run R of vessel V is prevented from entering branch B2.

An interventional guidewire is now advanced through catheter 104 into or beyond the region of interest of branch B2. Optionally, catheter 30, 40, or 70 is advanced through working channel 106 into or adjacent to branch B2 either before, during, or after advancement of the interventional guidewire. Interventional devices such as angioplasty balloon catheters, stent delivery systems, and the like are advanced along the interventional guidewire and used to treat the region of interest of branch B2. Embolic debris generated during treatment, if any, remains in the vicinity of the treatment area because there is no flow in branch B2 to transport the embolic material from the treatment area. Interventional devices are removed after treatment.

An aspiration device, for example a syringe, preferably at least 30 cc capacity, is used to draw a vacuum and aspirate emboli from the vicinity of the treatment area proximally through working channel 106 into the aspiration device. Alternatively, the aspiration device can be attached to the hub of catheter 30, 40, or 70 (if used) and emboli can be aspirated from the vicinity of the treatment area proximally through catheter 30, 40, or 70. Catheter 30, 40, or 70 may be moved proximally and distally in the region of interest while aspiration is being applied to vacuum emboli from the region of interest.

After aspiration of emboli from the region of interest, catheter 30, 40, or 70 can be removed, expandable structure 102 can be unexpanded by advancing sheath 110 over catheter 104, causing expandable structure 102 and catheter 104 to enter the sheath. Sheath 110 causes the curvature of catheter 104 to be straightened as catheter enters sheath. As embolic protection system 100 is collapsed into sheath 110, flow into branch B2 is restored. Embolic protection system 100 can thereafter be removed from the patient.

FIGS. 9A to 9F illustrate conceptually an alternative embodiment of an embolic protection system in accordance with the present invention. Embolic protection system 120 is comprised of expandable structure 122 and catheter 124 having working channel 126 and sheath 130. Catheter 124 can be comprised of polymers including but not limited to PEBAX®, polyethylene, nylon, polyester, and other materials known in the art, and may be made by processes known by those skilled in the art, such as extrusion. Preferably, catheter 124 is torquable and comprises metal reinforcement, for example braided wire. Working channel 126 is dimensioned to slideably receive interventional devices such as guidewires, balloon catheters, stent delivery systems with stents mounted thereon, atherectomy catheters, embolic protection devices such as distal embolic protection devices, thrombectomy devices, ultrasound catheters, aspiration catheters, and other devices (all not shown) known in the art and can have an internal diameter ranging from 0.012 inch to 0.200 inch (0.030 cm to 0.51 cm), more preferably from 0.040 inch to 0.110 inch (0.10 cm to 0.28 cm), more preferably from 0.060 inch to 0.096 inch (0.15 to 0.24 cm). In one preferred embodiment, working channel 126 has a diameter of 0.092 inch (0.23 cm). In another preferred embodiment, working channel 126 has a diameter of 0.070 inch (0.18 cm). A connector, for example a luer lock hub, may be attached to the proximal end of working channel 126 (not shown). One or more radiopaque marker bands 121 can be located on catheter 124 near the distal end of working channel 126. Radiopaque marker band 121 can comprise platinum, gold, tantalum, or other materials known in the art. Sheath 130 can be comprised of polymers including but not limited to PEBAX®, polyethylene, nylon, polyester, and other materials known in the art, and may be made by processes known by those skilled in the art, such as extrusion. Preferably sheath 130 is torqueable and comprises metal reinforcement, for example braided wire. Sheath 130 is dimensioned to slideably receive catheter 124 and expandable structure 122. Optionally, the distal portion of sheath 130 is keyed to catheter 124 by means of a key and keyway, linearly slideable non-circular cross sections, or other means (all not shown) to prevent the distal portion of sheath 130 from rotating in relation to catheter 124.

Expandable structure 122 is comprised of three or more sealing arms 131, membrane 132, and three or more support arms 135. Sealing arms 131 are attached to catheter 124 at or near marker band 121 using techniques such as bonding, welding, fusing, solvent bonding, ultrasonic welding, and the like. Sealing arms 131 are preferably made of self-expanding metal such as ELGILOY®, stainless steel, cobalt-chromium alloy, superelastic alloy, nitinol, or other materials as are known in the art. Sealing arms 131 may be wire, ribbon, sheet, composite, or other materials. In a preferred embodiment, sealing arms 131 are comprised of monofilament nitinol wires heat set in a curvilinear shape. Membrane 132 is permanently attached to sealing arms 131 and may be attached to outer surface of arm, inner surface of arm, between arms, or any combination thereof. Membrane 132 can be comprised of a thin and strong membranous material such as biaxially oriented nylon, polyester, PEBAX®, of thin flexible materials such as silicone, polyurethane, latex, and the like. In a preferred embodiment, membrane 132 is comprised of silicone polymer of 90 Shore A durometer or less and is attached to the outer surface of arm 131. Membrane 132 may be attached to a portion of or to all of sealing arms 131. In a preferred embodiment, membrane 132 is attached to sealing arms 131 in the region extending from marker band 131 to the distal tip of sealing arms 131. Support arms 135 are attached to catheter 124 at or near marker band 121 using techniques such as bonding, welding, fusing, solvent bonding, ultrasonic welding, and the like. In an alternative embodiment support arms 135 are attached to sealing arms 131. Support arms 135 are preferably made of self-expanding metal such as ELGILOY®, stainless steel, cobalt-chromium alloy, superelastic alloy, nitinol, or other materials as are known in the art. Support arms 135 may be wire, ribbon, sheet, composite, or other materials. In a preferred embodiment, support arms 135 are comprised of monofilament nitinol wires heat set in a curvilinear shape.

Figure 9A:
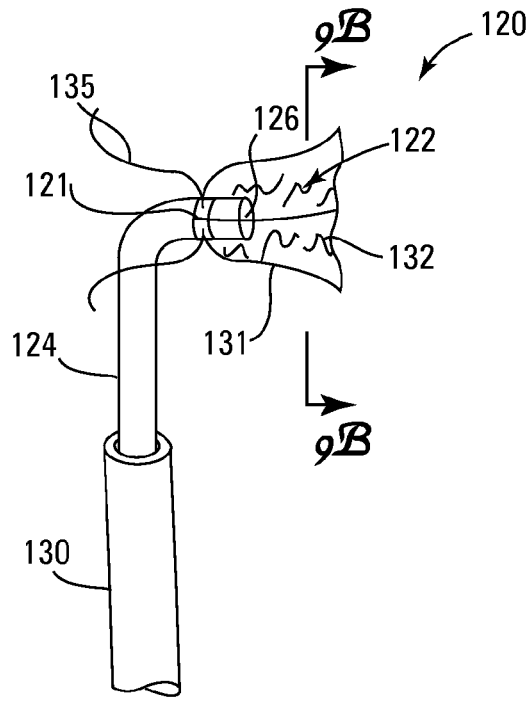
FIG. 9A illustrates conceptually an isometric diagram of an alternative embodiment of an embolic protection system in accordance with the present invention.
Figure 9B:
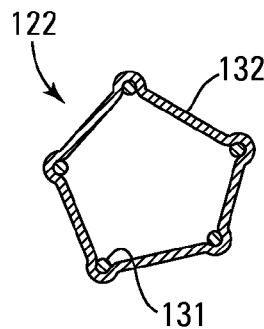
FIG. 9B illustrates conceptually a cross-sectional diagram of a component of an embolic protection system in accordance with the present invention.
Figure 9C:
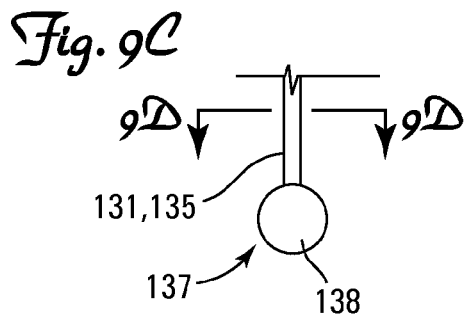
FIGS. 9C, 9D, 9E, and 9F illustrate conceptually side view or cross-sectional diagrams of components of an embolic protection system in accordance with the present invention.
Figure 9D:
Figure 9E:
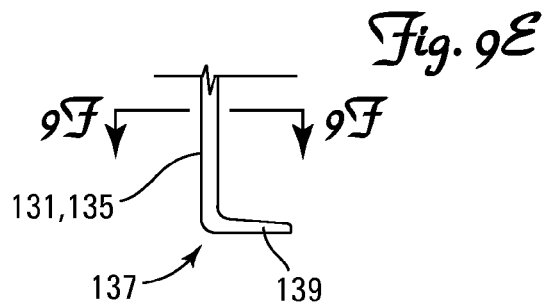
Figure 9F:
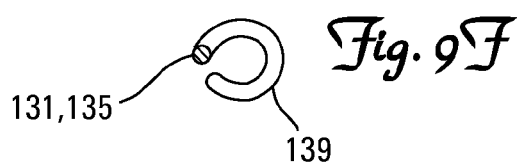

Optionally, some or all of sealing arms 131, some or all of support arms 135, or any combination thereof comprise pad 137 at the end thereof as shown in FIGS. 9C to 9F. Pad 137 distributes the force applied to vessel walls from arms 131, 135 and prevents or reduces the potential damage to vessel V caused by the ends of arms 131, 135. Pad 137 can comprise a ball 138 as shown in FIGS. 9C and 9D, can comprise a loop 139 as shown in FIGS. 9E and 9F, or can comprise other shapes provided the functional requirements of pad 137 are satisfied. Sealing arms 131 and support arms 135 must remain in position when deployed and resist forces caused by flow F in vessel V and may comprise anchors (not shown) on the surface of pad 137 or at ends of arms 131, 135 such as barbs, hooks, surface roughness, or other anchoring geometries as are known in the art.

Figure 10A:
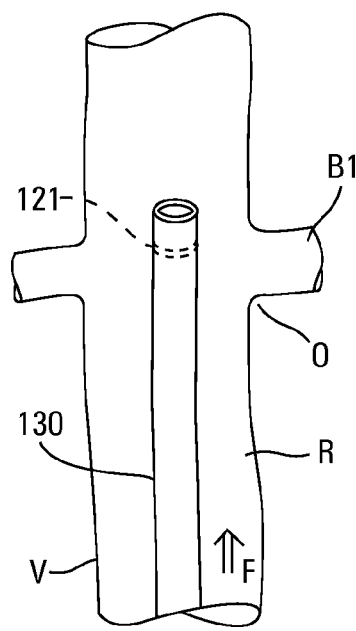
FIGS. 10A, 10B, 10C, and 10D illustrate conceptually a method of using an embolic protection system in accordance with the present invention.
Figure 10B:
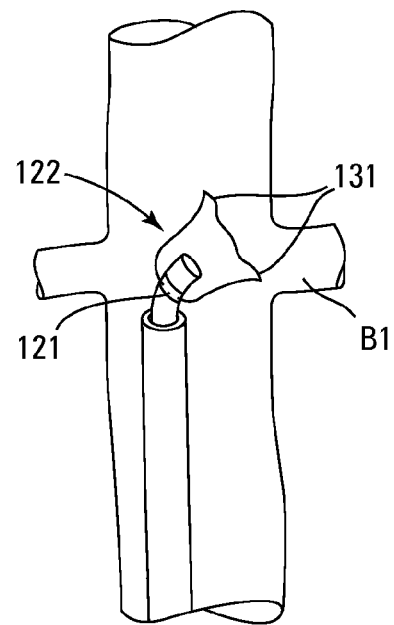
Figure 10C:
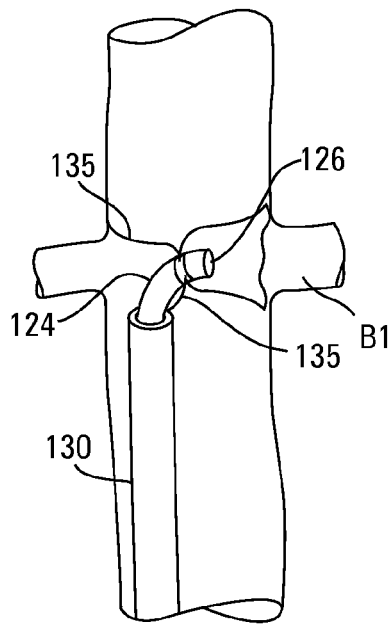

With reference to FIGS. 10A to 10D, one non-limiting exemplary method of using embolic protection system 120 in accordance with the present invention is now described. Embolic protection system 120 is introduced into the arterial vasculature using conventional techniques, advanced through the vasculature and positioned in run R of vessel V opposite branch B1. The position of system 120 is adjusted using images of marker band 121 as a guide until marker band 121 is located at a desired location such as opposite branch B1 (FIG. 10A). The distal most portion of expandable structure 122 and sealing arms 131 are then expanded by withdrawing sheath 130 relative to catheter 124 (FIG. 10B). Further withdrawal of sheath 130 relative to catheter 124 exposes at least some support arms 135 (FIG. 10C). Flow F will pass by catheter 124 allowing the catheter to be more accurately positioned since there will be few flow generated forces altering the position of system 120. Catheter 124, sheath 130, or both are then rotated by applying torsion on their respective shafts to assure that channel 126 is desirably aligned relative to branch B1. Radiographic contrast media can be injected through channel 126 to further ascertain orientation of catheter 124 tip relative to lumen of branch B1.

Figure 10D:
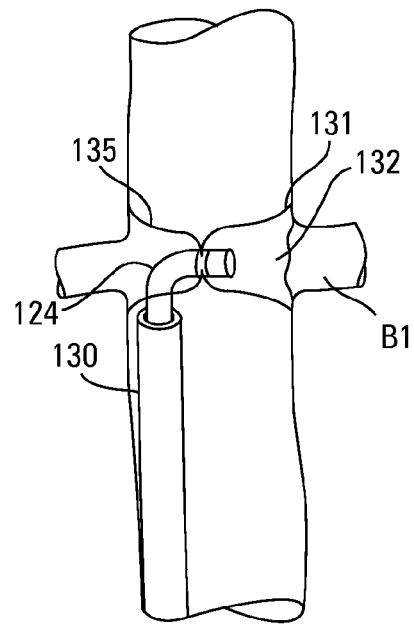

Once satisfied with orientation of catheter 124 tip relative to lumen of branch B1, sheath 130 is further withdrawn relative to catheter 124 until the proximal portion of expandable structure 122 is expanded and support arms 135 are fully outside of sheath 130, allowing membrane 132 to be pressed against the wall of vessel V (FIG. 10D). When both expandable structure 122 is expanded and membrane 132 abuts vessel V in region of ostium O of branch B1, flow F in run R of vessel V is prevented from entering branch B1.

An interventional guidewire is now advanced through catheter 124 into or beyond the region of interest of branch B1. Optionally, catheter 30, 40, or 70 is advanced through working channel 126 into or adjacent to branch B1 either before, during, or after advancement of the interventional guidewire. Interventional devices such as angioplasty balloon catheters, stent delivery systems, and the like are advanced along the interventional guidewire and used to treat the region of interest of branch B1. Embolic debris generated during treatment, if any, remains in the vicinity of the treatment area because there is no flow in branch B1 to transport the embolic material from the treatment area. Interventional devices are removed after treatment.

An aspiration device, for example a syringe, preferably at least 30 cc capacity, is used to draw a vacuum and aspirate emboli from the vicinity of the treatment area proximally through working channel 126 into the aspiration device. Alternatively, the aspiration device can be attached to the hub of catheter 30, 40, or 70 (if used) and emboli can be aspirated from the vicinity of the treatment area proximally through catheter 30, 40, or 70. Catheter 30, 40, or 70 may be moved proximally and distally in the region of interest while aspiration is being applied to vacuum emboli from the region of interest.

After aspiration of emboli from the region of interest, catheter 30, 40, or 70 can be removed, expandable structure 122 can be unexpanded by advancing sheath 130 over catheter 124, causing expandable structure 122 and catheter 124 to enter the sheath. Sheath 130 causes the curvature of catheter 124 to be straightened and causes arms 131, 135 to be straightened as they enter sheath 130. As embolic protection system 120 is collapsed into sheath 130, flow into branch B1 is restored. Embolic protection system 120 can thereafter be removed from the patient.

While this document has described an invention mainly in relation to vessel branch embolic protection, it is envisioned that the invention can be applied to other conduits in the body as well including arteries, veins, bronchi, ducts, ureters, urethra, and other lumens intended for the passage of air, fluids, or solids. The invention can be applied to any site of branching of an artery, vein, bronchus, duct, ureter, urethra, and other lumen including but not limited to the junction of the common, internal, and external carotid arteries, the junction of the main, left anterior descending, and circumflex coronary arteries, the junction of the left main or right coronary artery with the aorta, the junction of the aorta with the subclavian artery, and the junction of the aorta with the carotid artery. The embolic protection devices described herein are particularly well-suited for use in branched blood vessels, but they can also be used in straight blood vessels.

While the various embodiments of the present invention have related to embolic protection systems, the scope of the present invention is not so limited. Further, while choices for materials and configurations may have been described above with respect to certain embodiments, one of ordinary skill in the art will understand that the materials described and configurations are applicable across the embodiments.

The above description and the drawings are provided for the purpose of describing embodiments of the invention and are not intended to limit the scope of the invention in any way. It will be apparent to those skilled in the art that various modifications and variations can be made without departing from the spirit or scope of the invention. Thus, it is intended that the present invention cover the modifications and variations of this invention provided they come within the scope of the appended claims and their equivalents.

What is claimed is:

1. An embolic protection device for use during a surgical procedure in treating a patient's vasculature including first and second blood vessels intersecting one another at a juncture defining an ostium, the embolic protection device comprising:
    a catheter having proximal and distal ends, the catheter defining an internal working channel in communication with a working channel opening formed in a distal region of the catheter, the working channel and the working channel opening dimensioned to slideably receive an interventional device;
    a marker band supported by the catheter; and
    an expandable structure supported on the distal region of the catheter, the expandable structure comprising a sealing structure and a support structure, the support structure being connected to and extending proximally from the marker band such that the support structure is configured to contact the first blood vessel at a first location, and the sealing structure being connected to and extending distally from the marker band such that the sealing structure is configured to contact the first blood vessel at a second location opposite the first location adjacent the ostium to interfere with blood flow through the ostium, the working channel opening being configured and dimensioned to allow the interventional device to enter the second blood vessel.

2. The embolic protection device of claim 1, wherein the working channel opening is disposed within the sealing structure.

3. The embolic protection device of claim 1, wherein the expandable structure is self-expanding.

4. The embolic protection device of claim 1, wherein the working channel has an internal diameter of from 0.030 cm to 0.51 cm.

5. The embolic protection device of claim 1, wherein the working channel has an internal diameter of from 0.10 cm to 0.28 cm.

6. The embolic protection device of claim 1, wherein the working channel has an internal diameter of from 0.15 cm to 0.24 cm.

7. The embolic protection device of claim 1, wherein the device further comprises a retractable sheath that can be placed over the expandable structure.

8. The embolic protection device of claim 1, wherein the catheter has a curved distal portion.

9. The embolic protection device of claim 1, wherein the sealing structure is distal of the support structure.

10. The embolic protection device of claim 1, wherein the marker band includes a radiopaque material.

11. The embolic protection device of claim 1, wherein the sealing structure comprises three or more sealing arms and a membrane attached to the three or more sealing arms, and the support structure comprises three or more support arms.

12. The embolic protection device of claim 11, wherein the membrane is made of silicone polymer.

13. The embolic protection device of claim 11, wherein the sealing structure and the support structure are connected to the catheter at locations spaced approximately equidistant from the working channel opening.

14. The embolic protection device of claim 11, wherein the sealing structure is distal of the support structure.

15. The embolic protection device of claim 11, wherein the sealing arms are made of self-expanding metal.

16. The embolic protection device of claim 15, wherein the support arms are made of self-expanding metal.

17. The embolic protection device of claim 11, wherein at least one of the sealing arms comprises a pad at an end of the sealing arm.

18. The embolic protection device of claim 17, wherein the pad comprises a ball.

19. The embolic protection device of claim 17, wherein the pad comprises a loop.

20. The embolic protection device of claim 11, wherein at least one of the support arms comprises a pad at an end of the support arm.

21. The embolic protection device of claim 20, wherein the pad comprises a ball.

22. The embolic protection device of claim 20, wherein the pad comprises a loop.

23. A method for positioning an embolic protection device within a patient's vasculature, the method comprising:
    providing the embolic protection device of claim 1;
    advancing the embolic protection device to a target site within the patient's vasculature; and
    expanding the expandable structure within the patient's vasculature.

24. The method of claim 23, wherein the expandable structure is expanded in a first blood vessel, and stops blood flow through a second blood vessel and allows blood to flow through the first blood vessel, and the working channel opening is disposed to allow an interventional device to enter the second blood vessel.

25. The method of claim 24, wherein the interventional device is introduced into the second blood vessel and the blood in the second blood vessel is subsequently aspirated.

* * * * *